United States Patent [19]

Hall et al.

[11] Patent Number: 4,861,778
[45] Date of Patent: Aug. 29, 1989

[54] 2,3-DIHYDROPHTHALAZINE-1,4-DIONES

[75] Inventors: Iris H. Hall, Chapel Hill; Steven D. Wyrick, Durham, both of N.C.; James M. Chapman, Jr., Columbia, S.C.

[73] Assignee: Research Corporation, N.Y.

[21] Appl. No.: 874,939

[22] Filed: Jun. 16, 1986

[51] Int. Cl.$^4$ ............................................. A61K 31/495
[52] U.S. Cl. ................................... 514/248; 514/824
[58] Field of Search ............... 514/248, 237, 372, 824, 514/373

[56] References Cited

U.S. PATENT DOCUMENTS

| | | | |
|---|---|---|---|
| 2,420,702 | 5/1948 | Drewitt et al. | 260/569 |
| 2,453,578 | 11/1948 | Lacey et al. | 260/250 |
| 3,433,641 | 3/1969 | Margot | 99/2 |
| 3,497,512 | 2/1970 | Hofer et al. | 260/250 |
| 3,864,343 | 2/1975 | Inoue et al. | 260/250 P |
| 3,870,792 | 3/1975 | Inoue et al. | 424/250 |
| 3,963,716 | 6/1976 | Inoue et al. | 260/250 P |
| 4,226,993 | 10/1980 | Buckler et al. | 544/237 |
| 4,293,553 | 10/1981 | Ishikawa et al. | 424/250 |

OTHER PUBLICATIONS

Buu-Hoi et al., Rec. Trav. Chim., vol. 70, 1099–1104 (1951).
Offe et al., Zeit. Natur., vol. 7b, 446–462 (1952).
White et al., J. Org. Chem., 34:2462–2468 (1968).

Primary Examiner—Douglas W. Robinson
Assistant Examiner—R. Kearse
Attorney, Agent, or Firm—Scully, Scott, Murphy & Presser

[57] ABSTRACT

A compound having the structural formula

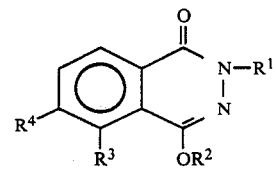

wherein $R^1$ is hydrogen, $C_1$–$C_6$ alkyl, $C_2$–$C_6$ carbalkoxyalkyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C_1$–$C_3$ alkyl, $C_1$–$C_3$ alkoxy or halogen with the provisos that if $R^2$, $R^3$ and $R^4$ are hydrogen, then $R^1$ is not methyl, n-propyl or phenyl substituted with methyl in the ortho or para position; if $R^1$, $R^2$ and $R^3$ are hydrogen then $R^4$ is not hydrogen, methyl or methoxy; and if $R^1$ and $R^2$ are both n-propyl or n-butyl then $R^3$ and $R^4$ are not both hydrogen. These compounds demonstrate utility as hypolipidemic agents.

The present invention is also directed to a process for controlling hyperlipidemia in mammals comprising treating mammals with a hyperlipidemia controlling effective amount of a compound having the above-identified structural formula wherein $R^1$ is hydrogen, $C_1$–$C_6$ alkyl, $C_2$–$C_6$ carboxyalkyl, $C_2$–$C_6$ carbalkoxyalkyl, phenyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C_1$–$C_3$ alkyl, $C_1$–$C_3$ alkoxy or halogen.

10 Claims, No Drawings

2,3-DIHYDROPHTHALAZINE-1,4-DIONES

BACKGROUND OF THE DISCLOSURE

1. Field of the Invention

The present invention is directed to a process for controlling hyperlipidemia. More specifically, the present invention is directed to a process for controlling hyperlipidemia in mammals by treating that condition with a generic class of 2,3-dihydrophthalazine-1,4-diones, the species of which include novel compounds.

2. Background of the Prior Art

Hyperlipidemia, a condition associated with elevated serum cholesterol, phospholipid and/or triglyceride blood levels, is the base cause of a whole class of illnesses which exact a terrible toll in death and infirmity as well economic loss associated with lost productive activity and expensive medical treatment. It is only necessary to mention one of the most serious conditions known in man, atherosclerosis, a hyperlipidemic induced illness, to appreciate the importance of developing treatment regimes effective in controlling this condition. Recent scientific studies indeed establish that coronary heart disease is related to blood lipid concentration. *J. Am. Med. Assn.*, Vol. 251, 351–373, Jan. 20, 1984; *N. Engl. J. Med.*, Vol. 314, 138–144, Jan. 16, 1986.

Because of the importance of hyperlipidemia, many compounds have been proposed to lower serum cholesterol, phospholipid and triglyceride blood levels in mammals. For example, U.S. Pat. No. 4,499,303 discloses a novel class of N-benzoyl, N-benzoylsulfamates and benzoylsulfonamides useful in this application.

Another class of compounds disclosed as useful in reducing serum cholesterol and triglyceride blood levels in mammals is set forth in U.S. Pat. No. 4,395,417. This patent describes the use of cyclic imides, diones, reduced diones and analogs thereof useful in this application.

Certain compounds within the generic class conveniently referred to as 2,3-dihydrophthalazine-1,4-diones are known in the art. N. T. Buu-Hoi et al., *Rec. Trav. Chim.*, Vol. 70, 1099–1104 (1951) disclose the use of 2,3-dihydro phthalazine-1,4-dione as a reactant with propyl halide or N-butyl halide in the presence of aqueous sodium hydroxide, to form 2-propyl-4-propoxyphthalazine-1(2H)-one and 2-butyl-4-butoxyphthalazine-1(2H)-one. Buu-Hoi et al. further teaches that these N,O-dialkyl products can be converted into 2-propyl-2,3-dihydrophthalazine-1,4-dione and 2-butyl-2,3-dihydrophthalazine-1,4-dione, respectively by treating the two above-reacted products with pyridinium hydrochloride. The Buu-Hoi et al. teaching is devoid of any suggestion that any of these synthesized compounds can be utilized for controlling hyperlipidemia.

U.S. Pat. No. 2,420,702, issued to Drewitt et al., describes a process for producing amino-hydrazines. In this process a byproduct of the reaction is 2,3-dihydrophthalazine-1,4-dione or a 3-hydrocarbyl substituted compound thereof. No disclosure is made of the utility of this byproduct.

U.S. Pat. No. 2,453,578, issued to Lacey et al. discloses a similar, albeit structurally distinguished, compound. This is 5-amino-1,4-dioxotetrahydrophthalazine which is recited to possess chemiluminescent activity. An intermediate in its production is 5-nitro-1,4-dioxotetrahydrophthalazine.

U.S. Pat. No. 3,433,641, issued to Margot, sets forth phthalazinone derivatives structurally similar to but outside the contemplation of the generic class of 2,3-dihydrophthalazine-1,4-diones utilized in the present invention. Margot states that these compounds have utility as growth-promoting additives for animal feed.

U.S. Pat. No. 3,497,512, issued to Hofer et al. teaches phthalazine derivatives which provide stability against ultraviolet radiation and heat. These compounds, distinguished from the compounds utilized in the process of the present invention, are formed from phthalazone derivatives similar to the compounds within the contemplation of the process of this invention.

A group of patents issued to Inoue et al., U.S. Pat. Nos. 3,864,343; 3,870,792; and 3,963,716, set forth phthalazone derivatives, structurally far removed from the compounds of the present invention. These patents are of interest because they are recited to prevent atherosclerosis. Inoue et al. states that this disease is prevented by inhibiting cholesterol deposition on arterial walls. The compounds of these patents are characterized by hydroxymethyl or substituted hydroxymethyl at the 1-position. The compounds of the present invention are all oxo-substituted at this position.

U.S. Pat. No. 4,226,993, issued to Buckler et al., sets forth a class of amino-functionalized phthalhydrazides. Not only are these compounds structurally distinguished by the substitutions on the fused phenyl ring but, in addition, are recited to have utility as intermediates in the synthesis of chemiluminescent phthalhydrazide-labeled conjugates.

U.S. Pat. No. 4,289,774, issued to Schacht et al. sets forth a class of compounds which in one embodiment is specifically a fused six-sided saturated ring. However, instead of an oxo substitution at the 4-position of the heterocyclic ring there is biphenyl, phenoxyphenyl, p-halobiphenyl or p-halophenoxyphenyl.

Finally, U.S. Pat. No. 4,293,553, issued to Ishikawa et al., describes 1-phthalazone derivatives useful for treating thrombotic disease. These compounds are either unsubstituted in the 1-position or 1-substituted with an alkyl or a hydroxymethyl group.

The above extensive analysis of the prior art is provided in order to establish that there is no disclosure of hypolipidemic agents whose structures are closely related to those of the present invention. Thus, there is no suggestion in the art for providing a new class of 2,3-dihydrophthalazine-1,4-diones useful in the treatment of hyperlipidemia.

SUMMARY OF THE INVENTION

It has now been discovered that a new class of compounds exhibits significant hypolipidemic activity in mammals at lower concentration than any of the compounds remotely similar thereto. These compounds are characterized by the ability to control hyperlipidemia at low concentrations thus eliminating many of the undesirable side effects found in the hypolipidemic agents of the prior art.

In accordance with the present invention a process is provided for controlling hyperlipidemia comprising the treatment of a mammal with a hyperlipidemia controlling effective amount of a compound having the structural formula

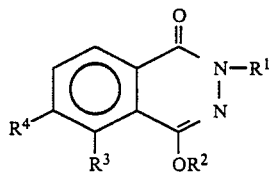

where $R^1$ is hydrogen, $C_1$–$C_6$ alkyl, $C_2$–$C_6$ carboxyalkyl, $C_2$–$C_6$ carbalkoxyalkyl, phenyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C_1$–$C_3$ alkyl, $C_1$–$C_3$ alkoxy or halogen.

In further accordance with the present invention a therapeutic composition is provided. This therapeutic composition comprises a hyperlipidemia controlling effective amount of a compound having the structural formula:

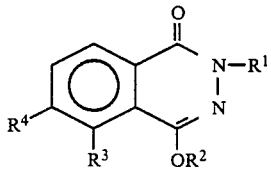

where $R^1$ is hydrogen, $C_1$–$C_6$ alkyl, $C_2$–$C_6$ carboxyalkyl, $C_2$–$C_6$ carbalkoxyalkyl, phenyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C_1$–$C_3$ alkyl, $C_1$–$C_3$ alkoxy or halogen and a pharmaceutically acceptable carrier therefor.

In still further accordance with the instant invention a compound having the structural formula:

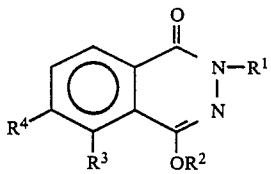

is provided wherein $R^1$ is hydrogen, $C_1$–$C_6$ alkyl, $C_2$–$C_6$ carbalkoxyalkyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C_1$–$C_3$ alkyl, $C_1$–$C_3$ alkoxy or halogen; with the provisos that if $R^2$, $R^3$ and $R^4$ are all hydrogen then $R^1$ is not methyl, n-propyl or phenyl substituted with methyl in the ortho or para position; if $R^1$, $R^2$ and $R^3$ are all hydrogen then $R^4$ is not hydrogen, methyl or methoxy; and if $R^1$ and $R^2$ are both n-propyl or n-butyl then $R^3$ and $R^4$ are not both hydrogen.

DETAILED DESCRIPTION

The compounds of the present invention have the structural formula:

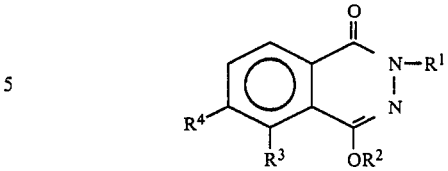

where $R^1$ is hydrogen, $C_1$–$C_6$ alkyl, $C_2$–$C_6$ carbalkoxyalkyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C_1$–$C_3$ alkyl, $C_1$–$C_3$ alkoxy or halogen; with the provisos that if $R^2$, $R^3$ and $R^4$ are all hydrogen then $R^1$ is not methyl, n-propyl or phenyl substituted with methyl in the ortho or para position; if $R^1$, $R^2$ and $R^3$ are hydrogen then $R^4$ is all hydrogen, methyl or methoxy; and if $R^1$ and $R^2$ are both n-propyl or n-butyl then $R^3$ and $R^4$ are both not hydrogen.

More preferably, the compound of the present invention has the structural formula (I) where $R^1$ is hydrogen, $C_1$–$C_5$ alkyl, $C_2$–$C_5$ carbalkoxyalkyl or phenyl substituted with $C_1$–$C_2$ alkyl or chlorine; $R^2$ is hydrogen or $C_1$–$C_5$ alkyl; and $R^3$ and $R^4$ are the same or different and are hydrogen, $C_1$–$C_2$ alkyl, $C_1$–$C_2$ alkoxy or chlorine. The provisos recited above in the broader definition of the compounds of the present invention apply in the preferred embodiment.

Still more preferably, the compound of the present invention has the stuuctural formula (I) wherein $R^1$ is hydrogen, $C_1$–$C_5$ alkyl, $C_3$–$C_4$ carbalkoxyalkyl or phenyl substituted with methyl or chlorine; $R^2$ is hydrogen or $C_1$–$C_5$ alkyl; and $R^3$ and $R^4$ are the same or different and are hydrogen, methyl, methoxy or chlorine. The provisos recited above also apply in this still more preferred embodiment of the compound of the present invention.

Yet still more preferably, the compound of the present invention is 2-ethyl-2,3-dihydrophthalazine-1,4-dione, 2-n-propyl-2,3-dihydrophthalazine-1,4-dione or 2-(4'-chlorophenyl)-2,3-dihydrophthalazine-1,4-dione.

Most preferably, the compound of the present invention is 2-(4'-chlorophenyl)-2,3-dihydrophthalazine-1,4-dione.

The instant invention also encompasses a process for controlling hyperlipidemia in mammals. In this process a mammal suffering from the diseases generically termed hyperlipidemia is treated with a hyperlipidemia controlling effective amount of a compound having the structural formula I wherein $R^1$ is hydrogen, $C_1$–$C_6$ alkyl, $C_2$–$C_6$ carboxyalkyl, $C_2$–$C_6$ carbalkoxyalkyl, phenyl or phenyl substituted with $C_1$–$C_3$ alkyl or halogen; $R^2$ is hydrogen or $C_1$–$C_6$ alkyl; $R^3$ and $R^4$ are the same or different and are hydrogen, $C_1$–$C_3$ alkyl, $C_1$–$C_3$ alkoxy or halogen.

More preferably, a process for controlling hyperlipidemia is provided wherein mammals suffering hyperlipidemia are treated with a hyperlipidemia controlling effective amount of a compound having the structural formula I wherein $R^1$ is hydrogen, $C_1$–$C_5$ alkyl, $C_2$–$C_5$ carboxyalkyl, $C_2$–$C_5$ carbalkoxyalkyl, phenyl or phenyl substituted with $C_1$–$C_2$ alkyl or chlorine; $R^2$ is hydrogen or $C_1$–$C_5$ alkyl; and $R^3$ and $R^4$ are the same or different and are hydrogen, $C_1$–$C_2$ alkyl, $C_1$–$C_2$ alkoxy or chlorine.

Still more preferably, a process for controlling hyperlipidemia in mammals is provided wherein mammals suffering hyperlipidemia are provided with a hyperlipidemia controlling effective amount of a compound having the structural formula I wherein $R^1$ is hydrogen, $C_1$–$C_5$ alkyl, $C_2$–$C_4$ carboxyalkyl, $C_2$–$C_4$ carbalkoxyalkyl, phenyl or phenyl substituted with methyl or chlorine; $R^2$ is hydrogen or $C_1$–$C_5$ alkyl; and $R^3$ and $R^4$ are the same or different and are hydrogen, methyl, methoxy or chlorine.

Yet still more preferably, a process for controlling hyperlipidemia is contemplated wherein a mammal suffering hyperlipidemia is treated with a hyperlipidemia controlling effective amount of a compound selected from the group consisting of 2,3-dihydrophthalazine-1,4-dione, 2-ethyl-2,3-dihydrophthalazine-1,4-dione, 2-n-butyl-2,3-dihydrophthalazine-1,4-dione, 6-methyl-2,3-dihydrophthalazine-1,4-dione, 2-(2′-carboxyethyl)-2,3-dihydrophthalazine-1,4-dione, 2-phenyl-2,3-dihydrophthalazine-1,4-dione and 2-(4′-chlorophenyl)-2,3-dihydrophthalazine-1,4-dione.

Yet more preferably, a process for controlling hyperlipidemia comprises treating a mammal suffering from hyperlipidemia with a hyperlipidemia controlling effective amount of a compound selected from the group consisting of 2,3-dihydrophthalazine-1,4-dione, 2-(2′-carboxyethyl)-2,3-dihydrophthalazine-1,4-dione, 2-phenyl-2,3-dihydrophthalazine-1,4-dione.

Even more preferably, the process for controlling hyperlipidemia includes treating a mammal with a hyperlipidemia controlling effective amount of a compound selected from the group consisting of 2,3-dihydrophthalazine-1,4-dione and 2-(2′-carboxyethyl)-2,3-dihydrophthalazine-1,4-dione.

Most preferably, the process of the present invention involves treating a mammal subject to hyperlipidemia with a hyperlipidemia controlling effective amount of 2-3-dihydrophthalazine-1,4-dione.

It is emphasized that the term hyperlipidemia refers to a whole host of mammalian diseases associated with elevated serum cholesterol, serum triglyceride and/or serum phospholipid blood levels. These conditions are oftentimes associated with a number of blood circulatory related diseases among which the most serious is atherosclerosis.

In a preferred embodiment of the process of the present invention a hyperlipidemia controlling effective amount of a compound, within the contemplation of the present invention, is provided by treating a hyperlipidemic mammal with a compound within the contemplation of this invention as defined above in a concentration of between about 5 and 60 milligrams per kilogram of mammalian body weight per day.

More preferably, a compound within the contemplation of the present invention is utilized in the process of the instant invention at a rate in the range of between about 10 and 40 milligrams per kilogram of mammalian body weight per day.

Most preferably, the hyperlipidemia controlling effective amount of a compound within the contemplation of the present invention is in the range of between about 15 and 30 milligrams per kilogram of mammalian body weight per day.

Another aspect of the present invention is provided by a pharmaceutical composition. The pharmaceutical composition of the present invention, useful in treatment of hyperlipidemia, comprises a compound having the structural formula I where $R^1$ is hydrogen, $C_1$–$C_6$ alkyl, $C_2$–$C_6$ carboxyalkyl, $C_2$–$C_6$ carbalkoxylalkyl, phenyl or phenyl substituted with $C_1$–$C_3$ alkyl or halogen; $R^2$ is hydrogen or $C_1$–$C_6$ alkyl; $R^3$ and $R^4$ are the same or different and are hydrogen, $C_1$–$C_3$ alkyl, $C_1$–$C_3$ alkoxy or halogen and a pharmaceutically acceptable carrier therefor.

More preferably, the composition of the present invention comprises a compound within the meaning of structural formula I where $R^1$ is hydrogen, $C_1$–$C_5$ alkyl, $C_2$–$C_5$ carboxyalkyl, $C_2$–$C_5$ carbalkoxyalkyl, phenyl or phenyl substituted with $C_1$–$C_2$ alkyl or chlorine; $R^2$ is hydrogen or $C_1$–$C_5$ alkyl; and $R^3$ and $R^4$ are the same or different and are hydrogen, $C_1$–$C_2$ alkyl, $C_1$–$C_2$ alkoxy or chlorine and a pharmaceutically acceptable carrier therefor.

Still more preferably, the pharmaceutical composition of the present invention comprises a compound having the structural formula defined by Compound (I) where $R^1$ is hydrogen, $C_1$–$C_5$ alkyl, $C_2$–$C_4$ carboxyalkyl, $C_2$–$C_4$ carbalkoxyalkyl, phenyl or phenyl substituted with methyl or chlorine; $R^2$ is hydrogen or $C_1$–$C_5$ alkyl; and $R^3$ and $R^4$ are the same or different and are hydrogen, methyl, methoxy or chlorine and a pharmaceutically acceptable carrier therefor.

Yet still more preferably, the pharmaceutical composition of the instant invention is a compound selected from the group consisting of 2,3-dihydrophthalazine-1,4-dione, 2-ethyl-2,3-dihydrophthalazine-1,4-dione, 2-n-propyl-2,3-dihydrophthalazine-1,4-dione, 6-methyl-2,3-dihydrophthalazine-1,4-dione, 2-(2′-carboxyethyl)-2,3-dihydrophthalazine-1,4-dione, 2-phenyl-2,3-dihydrophthalazine-1,4-dione and 2-(4′-chlorophenyl)-2,3-dihydrophthalazine-1,4-dione and a pharmaceutically acceptable carrier therefor.

Even more preferably, the pharmaceutical composition of this invention is a compound selected from the group consisting of 2,3-dihydrophthalazine-1,4-dione, 6-methyl-2,3-dihyrophthalazine-1,4-dione, 2-(2′-carboxyethyl)-2,3-dihydrophthalazine-1,4-dione and 2-phenyl-2,3-dihydrophthalazine-1,4-dione and a pharmaceutically acceptable carrier therefor.

Yet more preferably, the pharmaceutical composition of this invention is a compound selected from the group consisting of 2,3-dihydrophthalazine-1,4-dione, 2-phenyl-2,3-dihydrophthalazine-1,4-dione and 2-(2′-carboxyethyl)-2,3-dihydrophthalazine-1,4-dione and a pharmaceutically acceptable carrier therefor.

Most preferably, the pharmaceutical composition of the current invention is 2,3-dihydrophthalazine-1,4-dione and a pharmaceutically acceptable carrier therefor.

Pharmaceutically acceptable carriers within the contemplation of the present invention includes solvents, dispersion media, coatings, antibacterial and antifungal agents, isotonic and absorption delaying agents and the like. The use of such media and agents for pharmaceutically active substances is known in the art. Except in so far as any conventional medium or agent is incompatible with the active ingredient of the present invention its use in the hypolipidemic pharmaceutical composition of this invention is contemplated. Supplementary active ingredients can also be incorporated into the composition of the instant invention.

The composition of the present invention may be prepared for parenteral administration. When administered parenterally, that is, subcutaneously, intraperitoneally, intramuscularly or intravenously, the carrier may be water, buffered saline, ethanol, polyols, such as glycerol, propylene glycol or liquid polyethylene glycol, vegetable oils and the like.

To prevent microorganism contamination, the carrier of the composition of the present invention may include antibacterial and/or antifungal agents such as parabens, chlorobutanol, phenol, sorbic acid, thimersal and the like. In addition, isotonic agents, for example, glucose or sodium chloride, may also be included in the pharmaceutical carrier of the composition of the present invention.

In the case of parenterally administered hypolipidemic compositions it is especially advantageous to formulate the composition in dosage units. Such formulation provides a uniform dosage thus improving active agent administration. Dosage unit means the physically discrete unit suited for unitary administration. That is, each unit contains a predetermined amount of active material calculated to produce the desired hypolipidemic effect in association with the required pharmaceutical carrier. The actual dosage unit of the composition of this invention is dictated by and directly dependent upon the unique characteristics of the active material of the instant invention and the particular hypolipidemic effect to be achieved. It is within the skill of the physician to determine the exact dosage for the subject involved.

In addition to the carriers discussed above for use in parenteral administration, additional carriers may be utilized in orally administered compositions. Carriers for orally administered pharmaceutically acceptable compositions include ingredients useful in the formation of tablets or capsules. Among the pharmaceutically acceptable carriers suitable for orally administered compositions are such excipients as starch, milk, sugar, clays and the like. The tablet or capsule carrier may include an enteric coating to make such tablet or capsule resistant to the acid and digestive enzymes of the stomach.

Although any of the pharmaceutically acceptable carriers discussed above may be combined with the active compound of the present invention, a particularly preferred carrier is carboxymethylcellulose (CMC). Specifically, a 1 percent aqueous solution of CMC is preferred for use as the carrier of the composition of the present invention.

Still another aspect of the present invention is the process for forming the compounds of the present invention. In the case where N-monoalkyl derivatives are formed, these compounds are made in accordance with a process wherein 2,3-dihydrophthalazine-1,4-dione is treated with one equivalent of sodium hydride and a $C_1$–$C_6$ alkyl halide to produce the desired 2-alkyl-2,3-dihydrophthalazine-1,4-dione in good yield. The use of a unit equivalent of these reactants produces an undesired trace amount of the N,O-dialkyl product. To insure against the formation of this undesired side product, it has been found that the reaction of the above mentioned dione with excess sodium hydride and alkyl halide results in the formation of the 2-alkyl-4-alkoxyphthalazine-1(2H)-one exclusively.

In those instances where the substitution at the 2-position is phenyl or substituted phenyl, these compounds are obtained by reacting phthalic anhydride and substituted phenylhydrazine hydrochloride in absolute ethanol in accordance with the procedure set forth by Biguard et al., *Bull. Soc. Chim.*, Vol. 9, 675–689 (1942).

The carboxyalkyl carbalkoxyalkyl and oxoalkyl substituted compounds are obtained by reacting 2,3-dihydrophthalazine-1,4-dione with methyl acrylate and methyl vinyl ketone, respectively.

Those compounds having substitutions at the 5- and 6-position on the fused phenyl ring are prepared by treating 3- and 4-substituted phthalic anhydrides, respectively with 1 mole of hydrazine hydrate.

The following examples are given to illustrate the scope of the present invention. Because these examples are given for illustrative purposes only, the invention embodied herein should not be limited thereto.

EXAMPLE 1

Preparation of 2-Ethyl-2,3-Dihydrophthalazine-1,4-Dione (Compound No. 4)

2,3-Dihydrophthalazine-1,4-dione (0.02 mol) was added to a suspension of sodium hydride (0.02 mol; 50% suspension in mineral oil) in anhydrous dimethylformamide (100 ml). This was followed by the slow addition thereto of ethyl iodide (0.03 mol). The resulting mixture was stirred under reflux for 24 hours. The solvent was thereafter evaporated under vacuum and the resultant solid product was recrystallized from methanol.

The resulting product, 2-ethyl-2,3-dihydrophthalazine-1,4-dione, was obtained in a yield of 52 percent. The melting point of this compound, determined by using a Thomas-Hoover melting point apparatus, was 151–153° C.

A summary of this example is included in Table I.

EXAMPLE 2

Preparation of Compound Nos. 2, 6, 8 and 10

The procedure of Example 1 was repeated but for the substitution of ethyl iodide (0.03 mol) with methyl iodide, n-propyl iodide, n-butyl iodide and n-pentyl iodide respectively all added in a concentration of 0.03 mol. These compounds were treated in accordance with the procedure of Example 1 and were recrystallized from methanol, chloroform, ethanol and chloroform, respectively, to produce Compounds 2, 6, 8 and 10.

The melting points of these compounds, of which Compounds 8 and 10 are new, are summarized in Table I below. Again, melting temperatures were determined by using a Thomas-Hoover apparatus. The yield of these compounds is also set forth in Table I.

EXAMPLE 3

Preparation of 2-Methyl-4-Methoxyphthalazine-1(2H)-One (Compound No. 3)

2,3-Dihydrophthalazine-1,4-dione (0.02 mol) was added to a suspension of sodium hydride (0.04 mol; 50% solution in mineral oil) in anhydrous dimethylformamide (100 ml). To this was slowly added an excess amount of methyl iodide (0.05 mol). The mixture was stirred under reflux for 24 hours. The solvent was evaporated and the product purified by recrystallization from benzene. The purified product was obtained in a yield of 78 percent.

The melting point, obtained by utilizing a Thomas-Hoover melting point apparatus, was found to be 93°–96° C. This example is summarized in Table 1 below.

EXAMPLE 4

Preparation of Compound Nos. 5, 7, 9 and 11

Example 3 was repeated except for the substitution of methyl iodide (0.05 mol) with ethyl iodide, n-propyl iodide and n-butyl iodide all at a concentration of 0.05 mol, to produce Compounds 5, 7, 9 and 11, respectively. Compound 5 was recrystallized in accordance with the procedure of Example 3. However, Compound 7, 9 and 11 were purified over a column of silica gel using chloroform:ethyl acetate (1:1).

The results of these synthesis, including yield and melting point data, obtained by utilizing a Thomas-Hoover melting point apparatus, is included in Table 1.

EXAMPLE 5

Preparation of
5-Chloro-2,3-Dihydrophthalazine-1,4-Dione
(Compound No. 12)

A mixture of 3-chlorophthalic anyhydride (0.02 mol) and hydrazine hydrate (0.02 mol) in dry ethanol (50 ml) was heated to reflux in a reaction flask. Reflux continued for several hours until the 3-chlorophthalic anhydride disappeared and a white crystalline solid deposited on the walls of the flask. The solid was filtered and recrystallized from ethanol to yield 5-chloro-2,3-dihydrophthalazine1,4-dione in a yield of 58 percent.

The melting point, obtained by utilizing a Thomas-Hoover melting point apparatus, was above 300° C. The details of this example are included in Table 1.

EXAMPLE 6

Preparation of Compound Nos. 13-17

Example 5 was repeated but for the substitution of 4-chlorophthalic anhydride, 3-methylphthalic anhydride, 4-methylphthalic anhydride, 3-methoxyphthalic anhydride and 4-methoxyphthalic anhydride for the 3-chlorophthalic anhydride of Example 5 to prepare Compound Nos. 13-17, respectively.

A summary of these syntheses is provided in Table I.

EXAMPLE 7

Preparation of
2-(2'-Carboxyethyl)-2,3-Dihydrophthalazine-1,4-Dione
(Compound No. 18)

2,3-Dihydrophthalazine-1,4-dione(8.1 g; 0.05 mol) was suspended in 100 ml of absolute ethanol containing a catalytic amount of sodium ethoxide. Ethyl acrylate (5.0 g; 0.05 mol) was added to the suspension and the mixture was reacted under reflux for 42 hours. The hot reaction mixture was filtered and the solvent removed in vacuo. The product thus formed was dissolved in sodium hydroxide (0.07 M; 250 ml) and stirred overnight. The solution was acidified by the addition of hydrogen chloride resulting in the formation of a white crystalline solid. The solid was recrystallized from water to produce the product, 2-(2'-carboxyethyl)-2,3-dihydrophthalazine-1,4-dione.

The product had a melting point of 201°-203° C. and was recovered in a yield of 26%. This example is summarized in Table I.

EXAMPLE 7A

Preparation of
2-(1'-Carbethoxymethyl)-2,3-Dihydrophthalazine-1,4-Dione (Compound No. 19)

A mixture of sodium hydride (0.05 g; 0.01 mol; 50% suspension in mineral oil); 2,3-dihydrophthalazine-1,4-dione (1.6 g; 0.01 mol); and ethylbromoacetate (excess) in anhydrous dimethylformamide (50 ml) was refluxed for 24 hours. The dimethylformamide solvent was then evaporated affording a gummy material. This gummy material was purified over column silica gel using chloroform: ethyl acetate (1:1) to obtain the product, 2-(1'-carbethoxymethyl)-2,3-dihydrophthalazine-1,4-dione.

The pure product, recrystallized from ethanol, had a melting point of 68°-70° C. and was obtained in a yield of 10%. This example is summarized in Table I.

EXAMPLE 8

Preparation of
2-(3'-Oxobutyl)-2,3-Dihydrophthalazine-1,4-Dione
(Compound No. 20).

2,3-Dihydrophthalazine-1,4-dione (16.2 g; 0.1 mol) was suspended in 95 percent ethanol (200 ml). The suspension was heated to reflux and methyl vinyl ketone (8.4 g; 0.12 mol) was added to the refluxing suspension. With the ketone in the reaction mixture, the mixture was refluxed for 41 hours. The solid remaining after refluxing was filtered. The filtrate was concentrated to obtain the product which was crystallized from ethanol. The yield was determined to be 80 percent. The product had a melting point of 152°-153° C. A summary of this synthesis is included in Table I.

EXAMPLE 9

Preparation of
2-Phenyl-2,3-Dihydrophthalazine-1,4-Dione
(Compound No. 21)

A mixture of phthalic anhydride (0.02 mol) and phenyl hydrazine (0.04 mol) in 95 percent acetic acid (70 ml.) was heated to reflux for 24 hours in the presence of a catalytic amount of sodium acetate (0.4 g). Water was added to the mixture and the precipitate collected. The precipitate was washed with water, agitated with 2 percent aqueous solution of sodium hydroxide and filtered. The filtrate was acidified with concentrated hydrogen chloride. The precipitate was collected and recrystallized from ethyl acetate to produce the product, 2-phenyl-2,3-dihydrophthalazine-1,4-dione.

The product was obtained in a yield of 58 percent and had a melting point, as measured by a Thomas-Hoover melting point apparatus, of 207°-209° C.

This example is tabulated in Table I.

EXAMPLE 10

Preparation of Compound Nos. 22-27

The procedure of Example 9 was repeated but for the substitution of chlorophenyl hydrazine hydrochloride or methyl-phenyl hydrazine hydrochloride for the phenyl hydrazine of Example 9 and the recrystallization of the product from ethanol, rather than ethyl acetate.

The resultant products of these synthesis, the 2-chlorophenyl or 2-methylphenyl diones in the ortho, meta or para positions are summarized in Table 1 below.

TABLE I

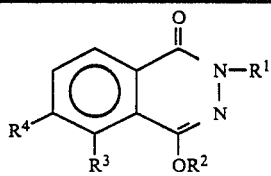

| Compd. No. | R$^1$ | R$^2$ | R$^3$ | R$^4$ | MP, °C. | Yield, % | Recrystallizing Solvent |
|---|---|---|---|---|---|---|---|
| 1 | H | H | H | H | — | — | None |
| 2 | CH$_3$ | H | H | H | 132–136$^a$ | 45 | Methanol |
| 3 | CH$_3$ | CH$_3$ | H | H | 93–96 | 78 | Benzene |
| 4 | C$_2$H$_5$ | H | H | H | 151–153 | 52 | Methanol |
| 5 | C$_2$H$_5$ | C$_2$H$_5$ | H | H | 71–73 | 73 | Benzene |
| 6 | n-C$_3$H$_7$ | H | H | H | 160–162 | 52 | Chloroform |
| 7 | n-C$_3$H$_7$ | n-C$_3$H$_7$ | H | H | —$^h$ | 70 | Chloroform:Ethyl Acetate |
| 8 | n-C$_4$H$_9$ | H | H | H | 95–96 | 48 | Ethanol |
| 9 | n-C$_4$H$_9$ | n-C$_4$H$_9$ | H | H | —$^h$ | 60 | Chloroform:Ethyl Acetate |
| 10 | n-C$_5$H$_{11}$ | H | H | H | 90–92 | 43 | Chloroform |
| 11 | n-C$_5$H$_{11}$ | n-C$_5$H$_{11}$ | H | H | — | 56 | Chloroform:Ethyl Acetate |
| 12 | H | H | Cl | H | 300 | 65 | Ethanol |
| 13 | H | H | H | Cl | 300 | 76 | Ethanol |
| 14 | H | H | CH$_3$ | H | 300 | 83 | Ethanol |
| 15 | H | H | H | CH$_3$ | 300$^b$ | 75 | Ethanol |
| 16 | H | H | OCH$_3$ | H | 236–240 | 68 | Ethanol |
| 17 | H | H | H | OCH$_3$ | 290–291$^c$ | 72 | Ethanol |
| 18 | CH$_2$CH$_2$COOH | H | H | H | 201–203$^d$ | 26 | Water |
| 19 | CH$_2$COOC$_2$H$_5$ | H | H | H | 68–70 | 10 | Ethanol |
| 20 | CH$_2$CH$_2$COCH$_3$ | H | H | H | 152–153 | 80 | Ethanol |
| 21 | C$_6$H$_5$ | H | H | H | 207–109$^e$ | 58 | Ethyl Acetate |
| 22 | o-Cl C$_6$H$_5$ | H | H | H | 213–215 | 54 | Ethanol |
| 23 | m-Cl C$_6$H$_5$ | H | H | H | 229–232 | 60 | Ethanol |
| 24 | p-Cl C$_6$H$_5$ | H | H | H | 251–252 | 67 | Ethanol |
| 25 | o-CH$_3$ C$_6$H$_5$ | H | H | H | 203–205$^f$ | 38 | Ethanol |
| 26 | m-CH$_3$ C$_6$H$_5$ | H | H | H | 218–220 | 52 | Ethanol |
| 27 | p-CH$_3$ C$_6$H$_5$ | H | H | H | 222–224$^g$ | 65 | Ethanol |

FOOTNOTES:
$^a$Literature Melting Point: 139–140° C.
$^b$Literature Melting Point: 300° C.
$^c$Literature Melting Point: 293° C.
$^d$Literature Melting Point: 206° C.
$^e$Literature Melting Point: 212° C.
$^f$Literature Melting Point: 207° C.
$^g$Literature Melting Point: 225° C.
$^h$Synthesized by Buu-Hoi et al. - No melting points

EXAMPLE 11

Hypolipidemic Activity of 2,3-Dihydrophthalazine-1,4-Diones in Normal Male Mice The compounds of Table I, Compounds 1–27, were suspended in an aqueous 1 percent carboxymethylcellulose (CMC) solution and homogenized. Each of the prepared compounds was administered intraperitoneally, in a dosage of 20 milligrams per kilogram of body weight per day, to a group of six CF$_1$ male mice, each weighing approximately 25 grams, for 16 days. On Days 9 and 16 blood was obtained from each of the tested mice by tail vein bleeding. The blood serum so obtained was separated by centrifugation for three minutes. Serum cholesterol levels were determined by a modification of the Leibermann-Burchard reaction, (Ness et al., Clin. Chem. Acta., Vol. 10, 229 [1964]). Serum triglyceride levels were obtained on Day 16 by use of the Bio-Dynamics/bm Triglyceride Kit.

In addition to the above-described treated mice, an untreated control group of six mice were similarly tested on Days 9 and 16 to determine their serum cholesterol and serum triglyceride blood levels. Based on the results obtained for the untreated control group, the percent control, based on serum cholesterol and serum triglyceride levels of the treated mice compared to the untreated mice, was obtained. Table II reports this percent control, including standard deviation, which indicates the level of confidence of these numbers.

TABLE II

| | PERCENT CONTROL, ± STANDARD DEVIATION | | |
|---|---|---|---|
| Compound No. | Serum Cholesterol | | Serum Triglyceride |
| | Day 9 | Day 16 | Day 16 |
| 1% CMC (Control) | 100 ± 5 | 100 ± 6 | 100 ± 5 |
| 1 | 53 ± 4 | 49 ± 5 | 57 ± 4 |
| 2 | 72 ± 5 | 77 ± 3 | 66 ± 4 |
| 3 | 84 ± 6 | 81 ± 5 | 64 ± 5 |
| 4 | 71 ± 7 | 58 ± 5 | 59 ± 4 |
| 5 | 77 ± 5 | 76 ± 4 | 57 ± 3 |
| 6 | 77 ± 6 | 68 ± 5 | 62 ± 2 |
| 7 | 68 ± 3 | 69 ± 5 | 69 ± 2 |
| 8 | 59 ± 2 | 58 ± 3 | 73 ± 4 |
| 9 | 65 ± 4 | 61 ± 3 | 66 ± 3 |
| 10 | 74 ± 3 | 71 ± 5 | 55 ± 4 |
| 11 | 86 ± 6 | 63 ± 4 | 59 ± 3 |
| 12 | 72 ± 5 | 69 ± 4 | 86 ± 5 |
| 13 | 72 ± 4 | 64 ± 5 | 65 ± 4 |
| 14 | 80 ± 4 | 75 ± 3 | 73 ± 3 |
| 15 | 66 ± 8 | 55 ± 4 | 54 ± 4 |
| 16 | 82 ± 5 | 78 ± 3 | 81 ± 4 |
| 17 | 77 ± 5 | 76 ± 4 | 69 ± 3 |
| 18 | 54 ± 6 | 34 ± 3 | 60 ± 4 |
| 19 | 78 ± 6 | 69 ± 5 | 73 ± 4 |
| 20 | 72 ± 6 | 59 ± 3 | 70 ± 7 |
| 21 | 59 ± 5 | 58 ± 4 | 65 ± 3 |
| 22 | 72 ± 5 | 67 ± 3 | 68 ± 4 |
| 23 | 73 ± 4 | 62 ± 3 | 69 ± 5 |

TABLE II-continued

| Compound No. | PERCENT CONTROL, ± STANDARD DEVIATION | | |
|---|---|---|---|
| | Serum Cholesterol | | Serum Triglyceride |
| | Day 9 | Day 16 | Day 16 |
| 24 | 60 ± 3 | 54 ± 4 | 59 ± 5 |
| 25 | 82 ± 7 | 66 ± 5 | 76 ± 6 |
| 26 | 87 ± 6 | 74 ± 4 | 65 ± 3 |
| 27 | 89 ± 5 | 73 ± 6 | 57 ± 2 |

EXAMPLE 12

Hypolipidemic Effect of 2,3-Dihydrophthalazine-1,4-Dione (Compound No. 1)

The hypolipidemic effects of a preferred compound within the scope of the present invention, 2,3-dihydrophthalazine-1,4-dione (Compound No. 1), was tested in accordance with the procedure set forth in Example 11. However, in addition to testing normal $CF_1$ male mice at 20 mg/kg/d ip, sets of six of these mice were treated with dosages of 10, 40 and 60 mg/kg/d. A set of six mice were again treated with a 1 percent aqueous solution of CMC, the carrier for the active agent, as a control.

In addition, rats were treated with Compound No. 1. The rats used in the test were normal Sprague-Dawley male rats, each weighting approximately 350 grams. The rats, tested in groups of six, were orally administered 10 mg/kg/d of Compound 1 in an aqueous solution of 1 percent CMC. The treatment of 10 milligrams per kilogram of body weight per day continued for 14 days. On Days 7 and 14 blood was obtained from each of the rats by tail vein bleeding. The blood obtained was separated centrifugation for three minutes. Serum cholesterol and serum triglyceride blood levels were determined in accordance with the procedure of Example 1.

The results of both of these tests are summarized in Table III. In Table III the results are reported as percent of serum cholesterol and serum triglyceride based on the concentration of these materials found in the control, the rats treated with the 1 percent aqueous solution of CMC.

TABLE III

| | % CONTROL ± STANDARD DEVIATION | | | | | | |
|---|---|---|---|---|---|---|---|
| | $CF_1$ Male Mice | | | Sprague-Dawley Rats | | | |
| | Cholesterol | | Triglyceride | Cholesterol | | Triglyceride | |
| Treatment Regime | Day 9 | Day 16 | Day 16 | Day 7 | Day 14 | Day 7 | Day 14 |
| 1% CMC (Control) | 100 ± 6$^a$ | 100 ± 7$^b$ | 100 ± 6$^c$ | 100 ± 8$^d$ | 100 ± 7$^e$ | 100 ± 6$^f$ | 100 ± 7$^g$ |
| 2,3-Dihydrophthalazine-1,4-dione | | | | | | | |
| 10 mg/kg/day | 88 ± 5 | 76 ± 7* | 67 ± 5* | 75 ± 5 | 68 ± 8* | 66 ± 6* | 64 ± 5* |
| 20 mg/kg/day | 53 ± 4* | 49 ± 8* | 57 ± 4* | | | | |
| 40 mg/kg/day | 71 ± 7* | 60 ± 6* | 44 ± 3* | | | | |
| 60 mg/kg/day | 76 ± 8* | 55 ± 5* | 49 ± 5* | | | | |

Footnotes:
$^a$118 mg/dL
$^b$122 mg/dL
$^c$137 mg/dL
$^d$73 mg/dL
$^e$78 mg/dL
$^f$110 mg/dL
$^g$112 mg/dL
*p 0.001

EXAMPLE 13

Determination of Plasma Lipoprotein Fractions in Rats

Sets of six normal Sprague-Dawley male rats, each weighing approximately 350 grams, were orally treated with 10 milligrams per kilogram of body weight per day of 2,3-dihydrophthalazine-1,4-dione (Comp. No. 1) by intubation needle. In addition, a set of six Sprague-Dawley male rats of approximately the same weight were similarly treated except that the administered drug was the inert carrier, the 1 percent aqueous solution of CMC.

Blood was collected from all the rats participating in the test from the abdominal vein and lipoprotein fractions were obtained by the method of Hatch and Lees (Adv. Lipid Res., Vol. 6, 1 [1968]) and Havel et al. (J. Clin. Invest., Vol. 34, 1345 [1955]). Each of the fractions were analyzed for cholesterol in accordance with the Ness et al. test, for triglyceride level (Bio-Dynamic/bmc Triglyceride Kit), neutral lipids, in accordance with the test of Bragdon (J. Biol. Chem., Vol. 190, 513 [1951]), phospholipids, in accordance with the Stewart and Hendry procedure (Biochem. J., Vol. 29, 1683 [1935]) and protein levels, in accordance with the procedure of Lowry et al. (J. Biol. Chem., Vol. 193, 265 [1951]). The results of these tests are provided in Table IV.

TABLE IV

| | PERCENT CONTROL ± STANDARD DEVIATION | | | | |
|---|---|---|---|---|---|
| Chylomicrons | | | | | |
| Control (1% CMC) | 100 ± 5$^a$ | 100 ± 6$^b$ | 100 ± 7$^C$ | 100 ± 6$_d$ | 100 ± 5$^e$ |
| Treated (10 mg/kg/d Compd. 1) | 82 ± 6 | 85 ± 7 | 84 ± 8 | 92 ± 7 | 102 ± 6 |
| VLDL | | | | | |
| Control (1% CMC) | 100 ± 6$^f$ | 100 ± 6$^g$ | 100 ± 7$^h$ | 100 ± 7$^i$ | 100 ± 4$^j$ |
| Treated (10 mg/kg/d Compd. 1) | 30 ± 5* | 134 ± 10 | 81 ± 3 | 91 ± 6 | 103 ± 7 |
| LDL | | | | | |
| Control (1% CMC) | 100 ± 5$^k$ | 100 ± 6$^d$ | 100 ± 7$^m$ | 100 ± 6$^n$ | 100 ± 5$^o$ |
| Treated (10 mg/kg/d Compd. 1) | 35 ± 6* | 94 ± 7 | 88 ± 6 | 125 ± 7 | 92 ± 8 |
| HDL | | | | | |
| Control (1% CMC) | 100 ± 4$^p$ | 100 ± 5$^q$ | 100 ± 6$^r$ | 100 ± 6$^s$ | 100 ± 7$^t$ |

TABLE IV-continued

| PERCENT CONTROL ± STANDARD DEVIATION | | | | | |
|---|---|---|---|---|---|
| Treated (10 mg/kg/d Compd. 1) | 107 ± 3 | 42 ± 4* | 86 ± 3 | 42 ± 6* | 93 ± 7 |

Footnotes:
*P = 0.001; $^a$ = 337 μg/ml; $^b$ = 67 μg/ml; $^c$ = 420 μg/ml; $^d$ = 149 μg/ml; $^e$ = 184 μg/ml; $^f$ = 190 μg/ml; $^g$ = 98 μg/ml; $^h$ = 22 μg/ml; $^i$ = 25 μg/ml; $^j$ = 50 μg/ml; $^k$ = 210 μg/ml; $^l$ = 10 μg/ml; $^m$ = 45 μg/ml; $^n$ = 41 μg/ml; $^o$ = 122 μg/ml; $^p$ = 544 μg/ml; $^q$ = 620 μg/ml; $^r$ = 27 μg/ml; $^s$ = 153 μg/ml; $^t$ = 657 μg/ml

EXAMPLE 14

Effect of Compound 1 on Hyperlipidemic Mice

A group of CF$_1$ male mice were fed a diet resulting in induced hyperlipidemia. These mice, on average, had an elevated serum cholesterol level of 375 mg percent and an elevated serum triglycerides level of 367 mg/dl.

These hyperlipidemic mice were treated for 12 days with Compound 1 (2,3-dihydrophthalazine-1,4-dione) at a daily dosage of 20 mg/kg. At the conclusion of this treatment regime the average serum cholesterol level of the hyperlipidemic mice was lowered to 221 mg percent, a 41 percent reduction. Similarly, the average serum triglycerides level of the hyperlipidemic mice was reduced to 161 mg/dl, a reduction of 56 percent.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the scope of the present invention should be limited only by the appended claims.

What is claimed is:

1. A method for controlling hyperlipidemia in mammals comprising administering to a mammal in need thereof a hyperlipidemia controlling effective amount of a compound having the structural formula:

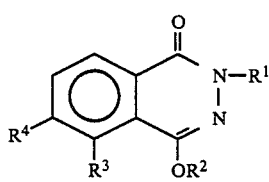

where $R^1$ is hydrogen, $C_1$–$C_6$ alkyl, $C_2$–$C_6$ carboxyalkyl, $C_2$–$C_6$ carbalkoxyalkyl, phenyl or phenyl substituted with $C_1$–$C_3$ alkyl or halogen; $R^2$ is hydrogen or $C_1$–$C_6$ alkyl; and $R^3$ and $R^4$ are the same or different and are hydrogen, $C^1$–$C_3$ alkyl, $C_1$–$C_3$ alkoxy or halogen.

2. A method in accordance with claim 1 wherein $R^1$ is hydrogen, $C_1$–$C^5$ alkyl, $C_2$–$C_5$ carboxyalkyl, $C_2$–$C_5$ carbalkoxyalkyl, phenyl or phenyl substituted with $C_1$–$C_2$ alkyl or chlorine; $R^2$ is hydrogen or $C_1$–$C_5$ alkyl; and $R^3$ and $R^4$ are the same or different and are hydrogen, $C_1$–$C_2$ alkyl, $C_1$–$C_2$ alkoxy or chlorine.

3. A method in accordance with claim 2 wherein $R^1$ is hydrogen, $C_1$–$C_5$ alkyl, $C_3$–$C_4$ carboxyalkyl, $C_3$–$C_4$ carbalkoxyalkyl, phenyl or phenyl substituted with methyl or chlorine; $R^2$ is hydrogen or $C_1$–$C_5$ alkyl; and $R^3$ and $R^4$ are the same or different and are hydrogen, methyl, methoxy or chlorine.

4. A method in accordance with claim 3 wherein said compound is selected from the group consisting of 2,3-dihydrophthalazine-1,4-dione, 2-ethyl-2,3-dihydrophthalazine-1,4-dione, 2-n-butyl-2,3-dihydrophthalazine-1,4-dione, 6-methyl-2,3-dihydrophthalazine-1,4-dione, 2-(2'-carboxyethyl)-2,3-dihydrophthalazine-1,4-dione, 2-phenyl-2,3-dihydrophthalazine-1,4-dione and 2-(4'-chlorophenyl)-2,3-dihydrophthalazine-1,4-dione.

5. A method in accordance with claim 4 wherein said compound is selected from the group consisting of 2,3-dihydrophthalazine-1,4-dione, 2-(2'-carboxyethyl)-2,3-dihydrophthalazine-1,4-dione and 2-phenyl-2,3-dihydrophthalazine-1,4-dione.

6. A method in accordance with claim 5 wherein said compound is selected from the group consisting of 2,3-dihydrophthalazine-1,4-dione and 2-(2'-carboxyethyl)-2,3-dihydrophthalazine-1,4-dione.

7. A method in accordance with claim 6 wherein said compound is 2,3-dihydrophthalazine-1,4-dione.

8. A method in accordance with claim 1 wherein said hyperlipidemia controlling effective amount of said compound is in the range of between about 5 and 60 milligrams per kilogram of mammalian body weight per day.

9. A method in accordance with claim 8 wherein said hyperlipidemia controlling effective amount of said compound is in the range of between about 10 and 40 milligrams per kilogram of mammalian body weight per day.

10. A method in accordance with claim 9 wherein said hyperlipidemia controlling effective amount of said compound is in the range of between about 15 and 30 milligrams per kilogram of mammalian body weight per day.

* * * * *